US012636196B2

(12) United States Patent
Kim et al.

(10) Patent No.: US 12,636,196 B2
(45) Date of Patent: May 26, 2026

(54) WOUND DRESSING PATCH

(71) Applicants:CHUNGNAM NATIONAL UNIVERSITY HOSPITAL, Daejeon (KR); THE INDUSTRY & ACADEMIC COOPERATION IN CHUNGNAM NATIONAL UNIVERSITY (IAC), Daejeon (KR)

(72) Inventors: Joo-Hak Kim, Daejeon (KR); Sang-Ha Oh, Daejeon (KR)

(73) Assignees: CHUNGNAM NATIONAL UNIVERSITY HOSPITAL, Daejeon (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 839 days.

(21) Appl. No.: 17/604,549

(22) PCT Filed: Apr. 17, 2020

(86) PCT No.: PCT/KR2020/005183
§ 371 (c)(1),
(2) Date: Oct. 18, 2021

(87) PCT Pub. No.: WO2020/213998
PCT Pub. Date: Oct. 22, 2020

(65) Prior Publication Data
US 2022/0192889 A1 Jun. 23, 2022

(30) Foreign Application Priority Data
Apr. 18, 2019 (KR) ......................... 10-2019-0045693

(51) Int. Cl.
A61F 13/0206 (2024.01)
A61F 13/0246 (2024.01)
A61L 15/22 (2006.01)

(52) U.S. Cl.
CPC ...... A61F 13/0206 (2013.01); A61F 13/0246 (2013.01); A61L 15/22 (2013.01)

(58) Field of Classification Search
CPC .. A61F 13/00; A61F 13/0206; A61F 13/0246; A61F 13/025; A61F 13/0263;
(Continued)

(56) References Cited

U.S. PATENT DOCUMENTS 4,784,653 A * 11/1988 Bolton ................ A61F 13/0223
602/50
2009/0148503 A1* 6/2009 Trieu ...................... A61B 17/42
424/447

FOREIGN PATENT DOCUMENTS

EP 3072533 A1 * 9/2016 ............. A61L 15/26
JP 2004-216098 A 8/2004
(Continued)

OTHER PUBLICATIONS

International Search Report issued on Aug. 7, 2020 in corresponding International application No. PCT/KR2020/005183; 7 pages.

*Primary Examiner* — Caitlin A Carreiro
(74) *Attorney, Agent, or Firm* — Maier & Maier, PLLC

(57) ABSTRACT
A wound dressing patch includes a backing film; an absorbent foam pad coupled to a portion of one surface of the backing film; an adhesive sheet provided on a remaining portion of the one surface of the backing film; and a lining material provided along a peripheral edge portion of the adhesive sheet and configured to impart a predetermined stiffness to the backing film. The lining material is spaced apart from the absorbent foam pad to surround the absorbent foam pad in a form of a substantially closed curve along the
(Continued)

peripheral edge portion of the adhesive sheet, and a distance between the lining material and an end of the adhesive sheet is shorter than a distance between the lining material and an edge of the absorbent foam pad.

7 Claims, 10 Drawing Sheets

(58) Field of Classification Search
  CPC ............. A61F 13/0226; A61F 13/0253; A61F
  13/00021; A61F 13/0259; A61F
  2013/00829; A61F 2013/00582; A61F
  2013/00089; A61L 15/22
  USPC ...................... 602/41–43, 46, 52, 54, 57, 58
  See application file for complete search history.

(56) References Cited

FOREIGN PATENT DOCUMENTS

| KR | 20-0357976 Y1 | 8/2004 | |
| KR | 10-2006-0095285 A | 8/2006 | |
| KR | 10-2013-0055561 A | 5/2013 | |
| KR | 20-2016-0000830 U | 3/2016 | |
| KR | 10-2047942 B1 | 11/2019 | |
| WO | WO-2008034897 A1 * | 3/2008 | ......... A61F 13/0203 |

* cited by examiner

WOUND DRESSING PATCH

FIELD

The present disclosure relates to a wound dressing patch.

BACKGROUND

A wound dressing patch is used to protect a wound and helps absorb an exudate coming from the wound.

Among conventional wound dressing patches, there have been proposed products including a silicon contact layer. These conventional products can be fixed without using a secondary adhesive plaster and can minimize secondary skin damage during dressing replacement. Therefore, the conventional products are particularly useful for bedsore patients with a weak skin. In addition, the conventional dressing patch products have a function of fixing a dressing patch to the wound of a patient and the vicinity thereof and a role of preventing a foreign substance including bacteria from being introduced between a wound dressing patch and a wound.

However, since the conventional dressing patch is attached to a skin of a patient, the patient may feel a sense of foreign object when an adhesive sheet included in the dressing patch is bonded to the skin of the patient. In addition, if the adhesive sheet has a predetermined stiffness or more, it may be difficult to be sticked with the skin due to the curvature of the skin of the patient. Therefore, in recent years, a thin adhesive sheet has been proposed to minimize the sense of foreign object felt by the patient and to improve the adhesive strength of the adhesive sheet. If the adhesive sheet is made thin, it is possible to improve the flexibility and adhesiveness of the adhesive sheet, and to minimize the sense of foreign object felt by the patient.

By the way, in the case of the conventional products in which the adhesive sheet is provided in a thin type, there is a problem in that the adhesive sheet is bonded and adhered to itself due to the increase in the flexibility of the adhesive sheet. In other words, when a release sheet (carrier film) attached to the bottom surface of the adhesive sheet is removed in order to bond the wound dressing patch to the lesion (the wound and its surroundings), a self-bonding phenomenon may undesirably occur in the flexible adhesive sheet. This leads to a problematic situation in which the patch becomes partially or wholly unusable and to be discarded. This situation may occur more frequently if antiseptic latex gloves are being worn to prevent contamination of the lesion.

Accordingly, there is a need for a study on a wound dressing patch with which the problem that the conventional adhesive sheet is curled up and adhered to itself, is minimized

SUMMARY

Embodiments of the present disclosure provide a wound dressing patch with an anti-folding function capable of maintaining the flexibility and adhesiveness of an adhesive sheet and preventing the adhesive sheet from curling up and sticking.

In accordance with an aspect of the present disclosure, there is provided a wound dressing patch, including: a backing film; an absorbent foam coupled to a portion of one surface of the backing film; an adhesive sheet provided on a remaining portion of the one surface of the backing film; and a lining material provided along a peripheral edge portion of the adhesive sheet and configured to impart a predetermined stiffness to the backing film, wherein the lining material is spaced apart from the absorbent foam pad to surround the absorbent foam pad in a form of a substantially closed curve along the peripheral edge portion of the adhesive sheet, and wherein a distance between the lining material and an end of the adhesive sheet is shorter than a distance between the lining material and an edge of the absorbent foam pad.

Further, the lining material may be provided in the adhesive sheet.

Further, the lining material may be disposed in the adhesive sheet so that an outer peripheral surface of the lining material is surrounded by the adhesive sheet.

Further, the lining material may be formed in a zigzag shape extending along the peripheral edge portion of the adhesive sheet.

Further, the lining material may include at least one curved portion.

Further, the lining material may be attached to the one surface of the backing film, and at least a portion of an outer peripheral surface of the lining material is accommodated in the adhesive sheet.

Further, the lining material may include at least one of a polymer selected from a group consisting of polyacrylamide, polypropylene, polyester, polyethylene, polyethylene terephthalate (PET), polystyrene, polyvinyl chloride (PVC) and polyacrylate, and a thermoplastic elastomer (TPE) for medical use.

In accordance with another aspect of the present disclosure, there is provided a wound dressing patch, including: a backing film; an absorbent foam pad coupled to the a portion of one surface of the backing film; an adhesive sheet provided on a remaining portion of the one surface of the backing film; and a lining material provided along a peripheral edge portion of the adhesive sheet and configured to impart a predetermined stiffness to the backing film, wherein the lining material is provided along the peripheral edge portion of the adhesive sheet while being spaced apart from the absorbent foam pad to surround the absorbent foam pad in a form of one of a dotted line, a dashed-dotted line, and a double-dotted line, and wherein a distance between the lining material and an end of the adhesive sheet is shorter than a distance between the lining material and an edge of the absorbent foam pad.

Further, the lining material may be provided in the adhesive sheet.

Further, the lining material may be disposed in the adhesive sheet so that an outer peripheral surface of the lining material is surrounded by the adhesive sheet.

Further, the lining material may be formed in a zigzag shape extending along the peripheral edge portion of the adhesive sheet.

Further, the lining material may include at least one curved portion.

Further, the lining material may be attached to the one surface of the backing film, and at least a portion of an outer peripheral surface of the lining material is accommodated in the adhesive sheet.

Further, the lining material may include at least one of a polymer selected from a group consisting of polyacrylamide, polypropylene, polyester, polyethylene, polyethylene terephthalate (PET), polystyrene, polyvinyl chloride (PVC) and polyacrylate, and a thermoplastic elastomer (TPE) for medical use.

In accordance with still another aspect of the present disclosure, there is provided a wound dressing patch, including: a backing film; an absorbent foam pad coupled to the a portion of one surface of the backing film; an adhesive sheet provided on a remaining portion of the one surface of the backing film; and a lining material provided along a peripheral edge portion of the adhesive sheet and configured to impart a predetermined stiffness to the backing film, wherein the lining material is spaced apart from the absorbent foam pad to surround the absorbent foam pad so that the lining material is formed symmetrically in portions of the peripheral edge portion of the adhesive sheet, and wherein a distance between the lining material and an end of the adhesive sheet is shorter than a distance between the lining material and an edge of the absorbent foam pad.

Advantageous Effects of the Disclosure

According to one embodiment of the present disclosure, it is possible to obtain the flexibility and adhesiveness of the adhesive sheet. In addition, the adhesive sheet is prevented from sticking even after the release sheet (carrier film) is removed for a bonding purpose. This enables a user to easily bond the adhesive sheet to a desired region without fail even in a state in which the user wears antiseptic latex gloves. Since the lining material is included in the adhesive sheet, it is possible to maintain the bonding force without changing the sense of thickness. Moreover, due to the intrinsic characteristics, the lining material remains without leaving a portion to be disposed (removed) before and after attaching the dressing patch. There, the dressing patch is capable of maintaining the same function even when re-bonding is performed. In addition, even when the dressing patch already attached to the wound is to be replaced, the lining material serves as a frame of the adhesive sheet. This facilitates attachment and detachment of the dressing patch, thereby reducing damage of the epidermis of the skin.

DETAILED DESCRIPTION OF THE EMBODIMENTS

Figure 1:
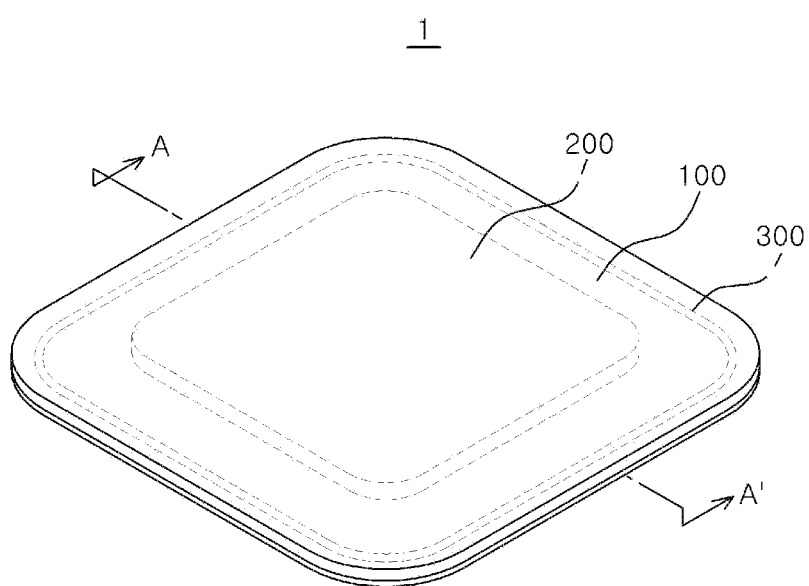
FIG. 1 is a perspective view of a wound dressing patch according to one embodiment of the present disclosure.

While the foregoing has described what are considered to be the best mode and/or other examples based on the principle that the inventor can properly define his own disclosure as the concept of the term, the terms and words used in the specification and claims described below shall not be interpreted in a conventional or dictionary sense, but shall be interpreted in terms of meaning and concepts conforming to the technical spirit of the present disclosure. Therefore, since the embodiments described in the specification and the configurations shown in the drawings are only the most preferred embodiments of the present disclosure, and do not represent all of the technical spirit of the present disclosure, it should be understood that there may be various equivalents and variations that could substitute them at the time of the present application.

Hereinafter, preferable embodiments of the present disclosure will be described in detail with reference to the accompanying drawings. It should be noted that the same component in the drawing is represented by the same symbol as possible. Further, a detailed description of the known function and configuration that may obscure the gist of this disclosure will be omitted. For the same reason, some components in the drawings are exaggerated, omitted or schematically illustrated, and the size of each component does not exactly reflect its actual size.

Further, in the present specification, the terms such as "upper", "lower", "side" and the like refer to directions in the drawings to which reference is made. Such terms can be differently expressed when a direction of a target is changed.

Figure 2:
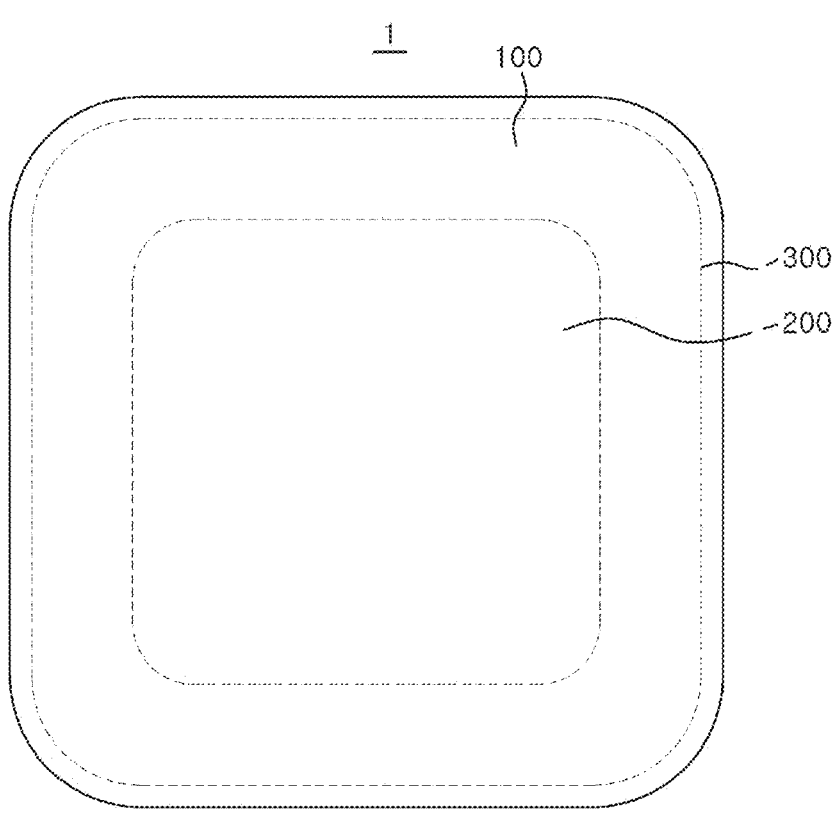
FIG. 2 is a plan view of the wound dressing patch according to one embodiment of the present disclosure.
Figure 3:
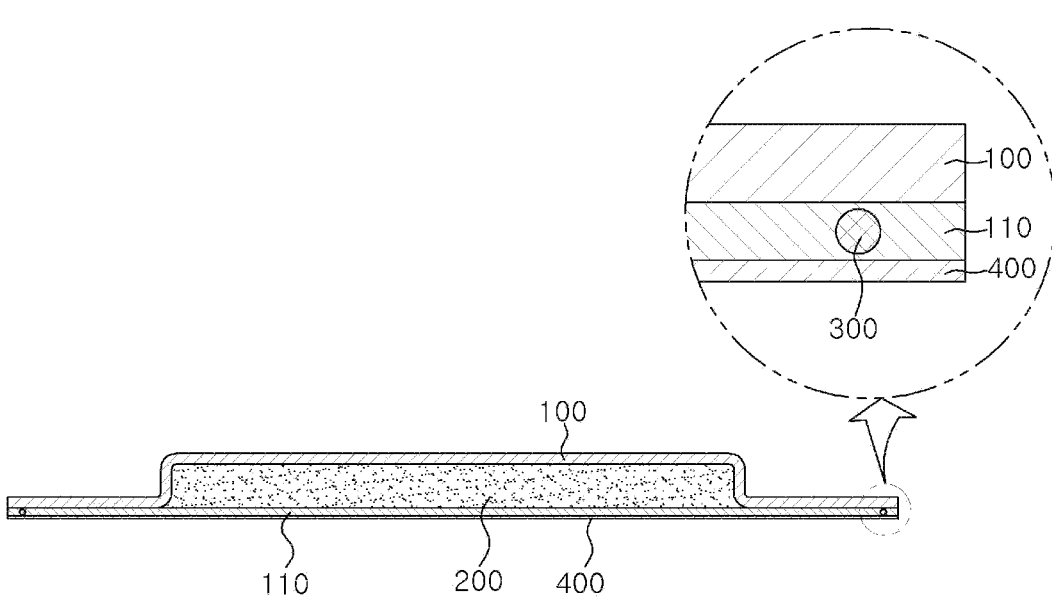
FIG. 3 is a side sectional view taken along line A-A' in FIG. 1.

FIG. 1 is a perspective view of a wound dressing patch according to one embodiment of the present disclosure. FIG. 2 is a plan view of the wound dressing patch according to one embodiment of the present disclosure. FIG. 3 is a side sectional view of the wound dressing patch according to one embodiment of the present disclosure.

Referring to FIGS. 1 to 3, the wound dressing patch 1 according to one embodiment of the present disclosure is used for the protection of a wound in a home or a hospital. The wound dressing patch 1 may include a backing film 100, an adhesive sheet 110 attached to one surface of the backing film 100, an absorbent foam pad 200 coupled to one surface of the backing film 100, and a lining material 300 provided along a peripheral edge portion of the adhesive sheet 110 and configured to have a predetermined stiffness so as to play a role of supporting the backing film 100.

The backing film 100 is a film constituting the opposite surface of the wound dressing patch 1 from the skin contact surface. The backing film 100 serves as a protective barrier against foreign substances including viruses and bacteria. The backing film 100 may be made of a material having a waterproof property, flexibility and stretchability. For example, the backing film 100 may be made of polyurethane, polyethylene, styrene-isoprene copolymer, styrene-butadiene block copolymer, polyvinylchloride, polyamide, or mixtures thereof. In addition, the backing film 100 may be made of a breathable material.

In addition, the adhesive sheet 110 coated with an adhesive agent may be provided on the one surface of the backing film 100. The adhesive sheet 110 may be provided to secure the adhesive force of the backing film 100, and may be made of, for example, terpene-based resin, xylene resin, silicone or the like. The adhesive sheet 110 is not limited to the proposed embodiment. Various adhesive materials commonly used in medical wound dressing patches may be used.

In addition, the adhesive sheet 110 may be made of a material through which an exudate discharged from a wound may pass. Accordingly, the exudate discharged from the wound when the wound dressing patch 1 is attached to the wound may pass through the adhesive sheet 110 and may be absorbed by the absorbent foam pad 200. However, this is merely an example, and the spirit of the present disclosure is not limited thereto. For example, the adhesive sheet 110 may be provided on the periphery of the absorbent foam pad 200 without overlapping the absorbent foam pad 200.

The absorbent foam pad 200 may be coupled to the one surface of the backing film 100. When the wound dressing patch 1 is bonded to the patient's skin, the absorbent foam pad 200 as thick foam may absorb and retain an exudate discharged from the wound, may provide an appropriate humid environment, and may protect a skin from external impact and irritation.

The absorbent foam pad 200 may be made of an absorbent material selected from a group consisting of hydrocolloid, hydrogel, polyurethane foam, polyacrylate, polyvinyl alcohol, polyvinyl pyrrolidone, an expandable synthetic polymer, a synthetic nonwoven material and a natural nonwoven material. When the absorbent foam pad 200 is made of hydrocolloid, the hydrocolloid may be, for example, calcium carboxymethylcellulose (CMC), pectin, gelatin, polymer carbowax, or carboxypolymethylene. However, the spirit of the present disclosure is not limited thereto. The absorbent foam pad 200 may be made of various materials commonly used in the medical industry for wound protection.

The lining material 300 may be provided to impart a predetermined stiffness to the backing film 100. The lining material may include at least one of a polymer such as polyacrylamide, polypropylene, polyester, polyethylene, polyethylene terephthalate (PET), polystyrene, polyvinyl chloride (PVC) or polyacrylate, and a thermoplastic elastomer (TPE) for medical use. To this end, the lining material 300 may be provided as, for example, a suture thread made of nylon, prolene or the like.

Figure 5A:
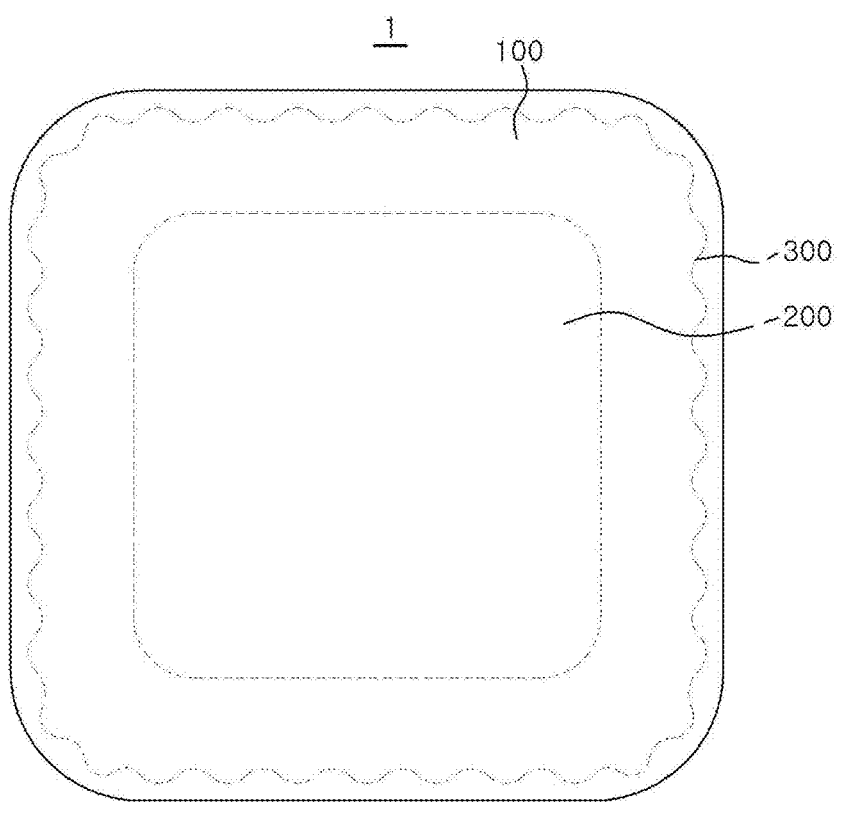
FIGS. 5A to 6D are plan views illustrating various patterns of a lining material provided in the wound dressing patch according to one embodiment of the present disclosure.
Figure 5B:
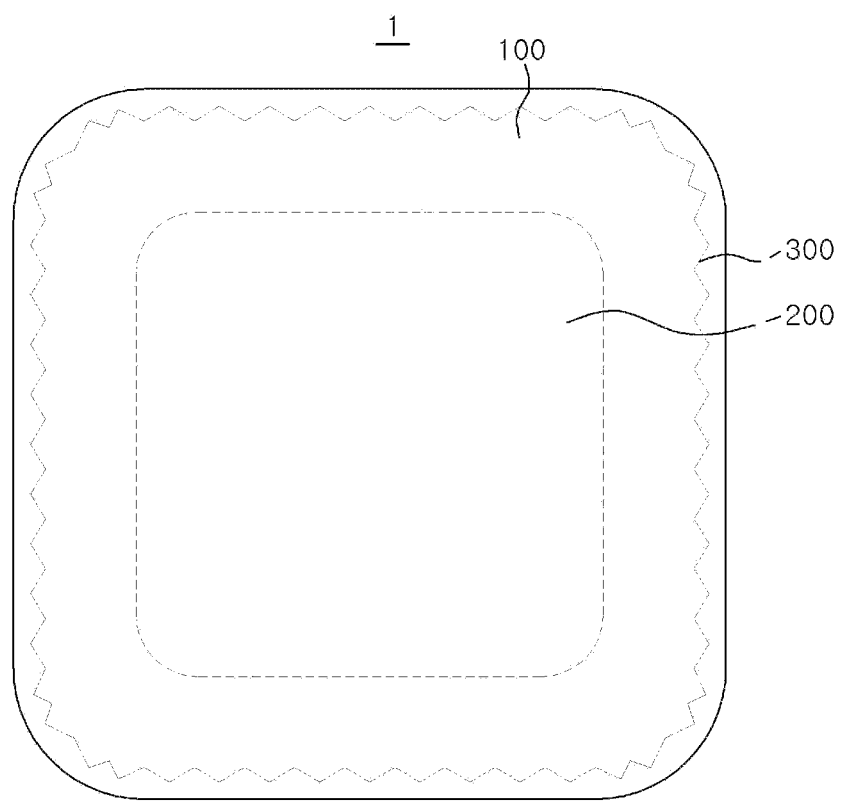

The lining material 300 may be provided along the peripheral edge portion of the adhesive sheet 110 while being spaced apart from the absorbent foam pad 200 to surround the absorbent foam pad 200, and may be formed into a substantially closed curve shape. Here, the substantially closed curve includes one continuous line forming a closed space, but also includes a case of forming a closed space as a whole using discontinuous points or lines. For example, the lining material 300 may be spaced apart from the foam pad 200 to surround the absorbent foam pad 200 along the periphery edge portion of the adhesive sheet 110 in the form of a dotted line as shown in FIG. 2, a dashed-dotted line as shown in FIG. 5B, a double-dotted line as shown in FIG. 5A, or the like.

In addition, the lining material 300 is spaced apart from the absorbent foam pad 200 and is symmetrically provided in a portion of the periphery edge portion of the adhesive sheet 110 in the form of a straight line, a curved line, or a substantially closed curve.

Figure 6A:
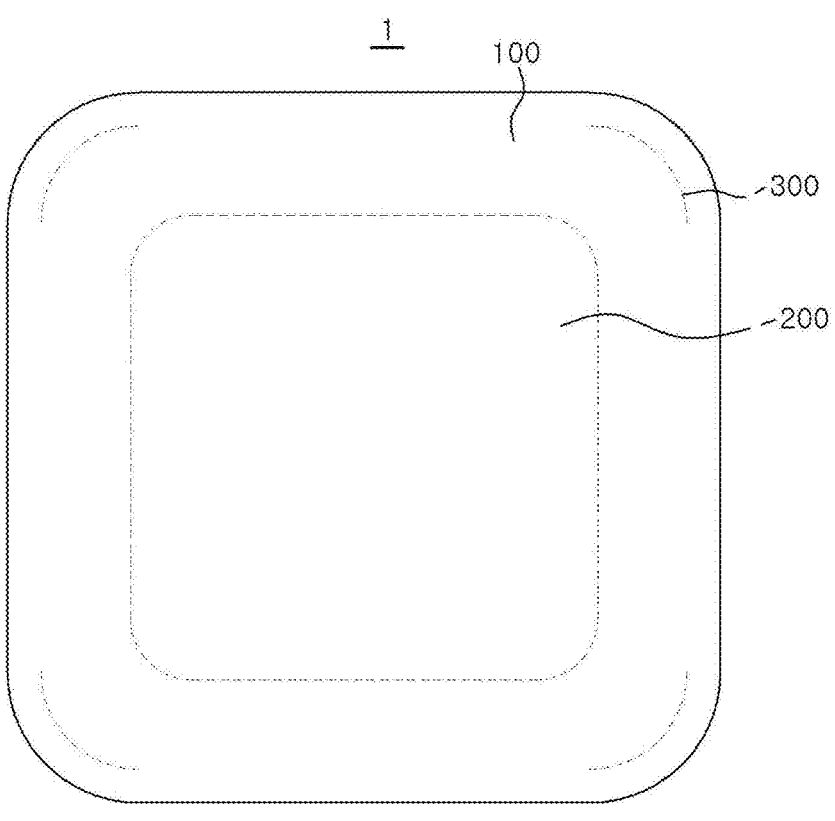
Figure 6B:
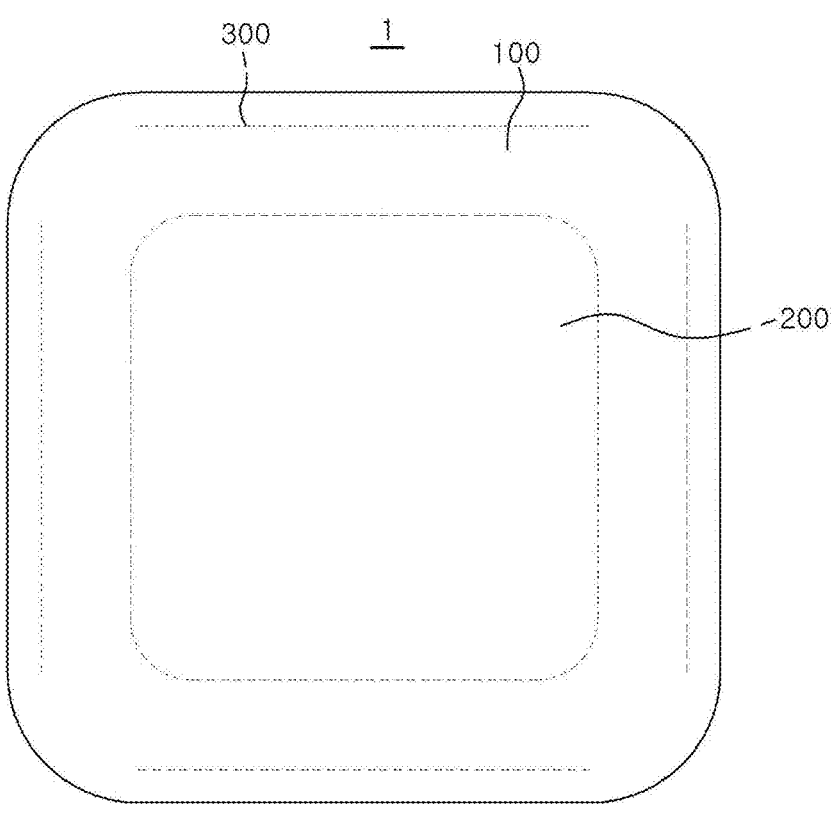
Figure 6C:
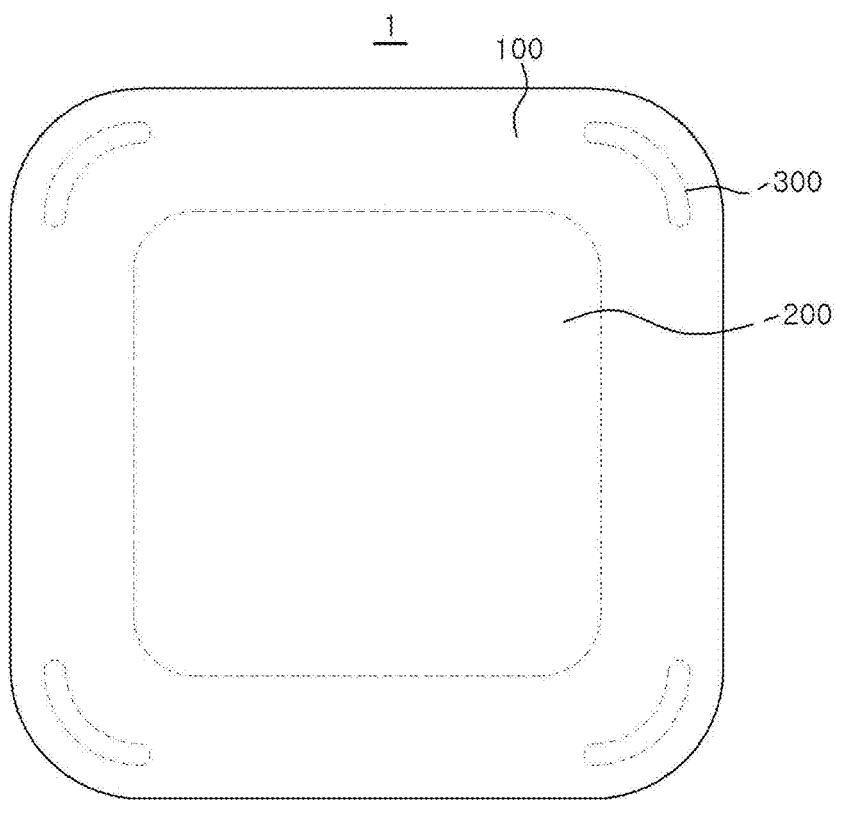
Figure 6D:
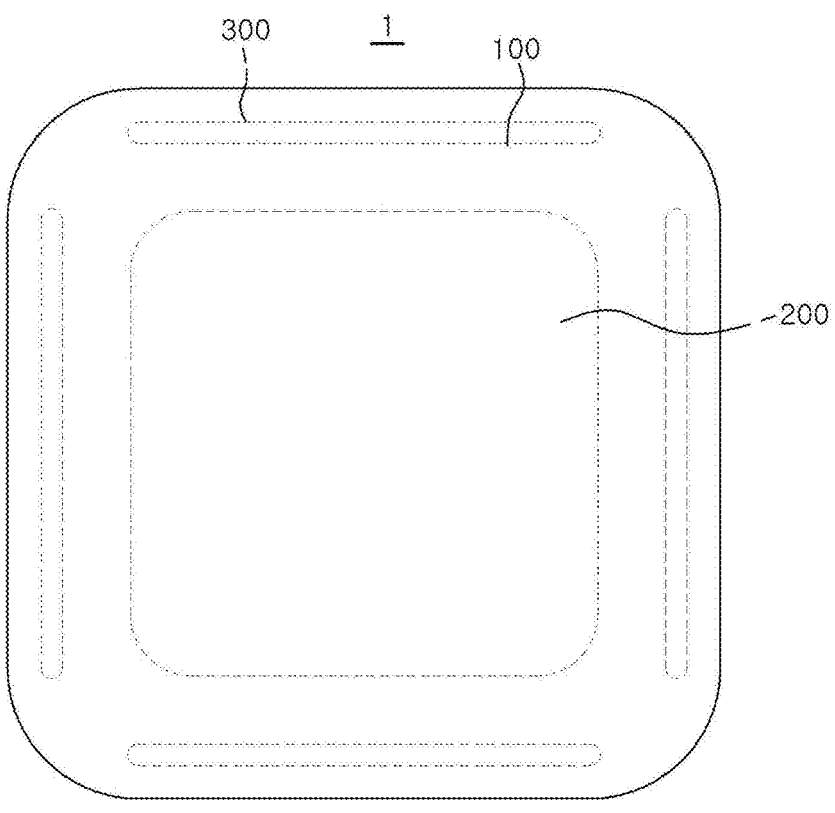

For example, as shown in FIG. 6A, the lining material 300 may be provided symmetrically while being spaced apart from the edge of the absorbent foam pad 200, or as shown in FIG. 6B, the lining material 300 may be provided symmetrically while being spaced apart from the four sides of the absorbent foam pad 200 in parallel. In addition, as shown in FIG. 6C, the lining material 300 may be spaced apart from the edge of the absorbent foam pad 200 in the form of a substantially closed curve, or, as shown in FIG. 6D, the lining material 300 may be provided in the form of a substantially closed curve spaced apart from the four sides of the absorbent foam pad 200 in parallel. Although the lining material 300 is shown as a dotted line in FIGS. 6A to 6D, the lining material 300 may be provided in a solid line, a chain line or other forms.

In this regard, the lining material 300 may be disposed close to the peripheral edge of the adhesive sheet 100 to prevent the adhesive sheet 110 from curling up. In other words, the distance between the lining material 300 and the edge of the adhesive sheet 110 may be shorter than the distance between the lining material 300 and the edge of the absorbent foam pad 200.

In addition, the lining material 300 may be provided inside the backing film 100 so as not to be exposed to the outside. For example, the lining material 300 may be disposed in the adhesive sheet 110 provided on the one surface of the backing film 100. As the lining material 300 is provided in the adhesive sheet 110, the thickness of the peripheral edge portion of the adhesive sheet 110 may be prevented from increasing by the lining material 300.

Figure 4:
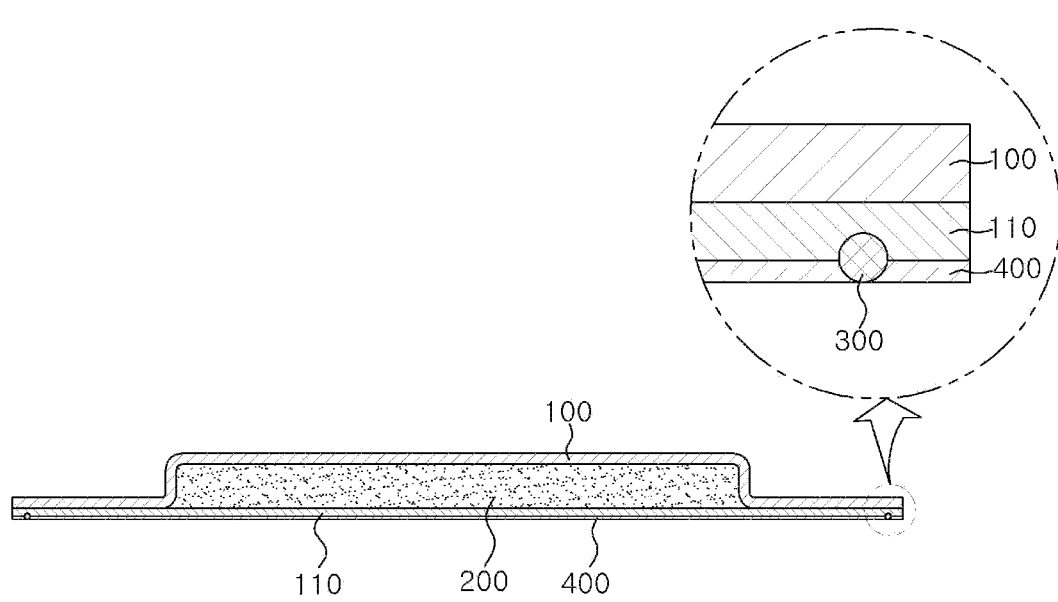
FIG. 4 is a side sectional view of a wound dressing patch, which is taken along line A-A' in FIG. 1, according to another embodiment of the present disclosure.

Meanwhile, the lining material 300 may be attached to one surface of the adhesive sheet 110 such that at least a portion of an outer peripheral surface of the lining material 300 is exposed to the outside of the adhesive sheet 110. In other words, referring to FIG. 4, the lining material 300 may be attached such that only a portion of the lining material 300 is accommodated in the adhesive sheet 110, and the portion of the lining material 300 exposed from the adhesive sheet 110 may be exposed to the outside when a release sheet (carrier film) 400 is removed. The exposed portion of the lining material 300 may have a stronger adhesive force than the adhesive sheet 110 existing around the lining material 300, which makes it possible to improve the adhesiveness around the wound. When the lining material 300 is attached and coupled to the one surface of the adhesive sheet 110 in this manner, the conventional wound dressing patch manufacturing process may be used as it is. Therefore, it is possible to simplify the manufacturing process and to reduce the manufacturing cost.

The lining material 300 may be provided in the adhesive sheet 110 in various shapes. For example, referring to FIG. 2, the lining material 300 may be provided in a shape corresponding to the shape of a peripheral edge portion of the absorbent foam pad 200 and the peripheral edge portion of the adhesive sheet 110. Alternatively, as shown in FIG. 5A, the lining material 300 may be provided in a wavy shape so as to include at least one curved portion. In addition, as shown in FIG. 5B, the lining material 300 may be provided in a zigzag shape. The shape of the lining material 300 coupled to the adhesive sheet 110 may be variously modified according to structural/design needs as long as it corresponds to a configuration capable of imparting a sufficient stiffness to the adhesive sheet 110.

The wound dressing patch 1 according to one embodiment of the present disclosure includes the lining material 300 that can impart a predetermined stiffness suitable to serve to support the backing film 100 as described above, whereby it is possible to prevent a phenomenon in which the adhesive sheet 110 is curled up and fixed to itself.

Meanwhile, a release sheet 400 may be attached to the one surface of the adhesive sheet 110. The release sheet 400 may be attached to the adhesive sheet 110 so as to cover the entirety of the one surface of the adhesive sheet 110. In addition, the release sheet 400 may be divided into a plurality of members. The release sheet 400 may be removed before using the wound dressing patch 1, and may prevent contamination of the adhesive sheet 110 and the absorbent foam pad 200. The first release sheet 400 is made of one or a combination of plastic, Mylar, PET and paper.

While the disclosure has been shown and described with respect to the embodiments, the present disclosure is not limited thereto. It will be understood by those skilled in the art that various changes and modifications may be made without departing from the scope of the disclosure as defined in the following claims.

What is claimed is:
1. A wound dressing patch, comprising:
a backing film;
an absorbent foam pad coupled to a portion of one surface
     of the backing film;

an adhesive sheet provided on a remaining portion of the one surface of the backing film, wherein the adhesive sheet is coated with an adhesive agent, and made of a material through which an exudate discharged from a wound passes; and a lining material provided along a peripheral edge portion of the adhesive sheet and configured to impart a predetermined stiffness to the backing film, wherein the lining material is at least partially embedded within the adhesive sheet without being embedded within the backing film and the absorbent foam pad, wherein the lining material is spaced apart from the absorbent foam pad in a radially outward direction to surround the absorbent foam pad in a form having a substantially closed curve along the peripheral edge portion of the adhesive sheet, wherein a distance between the lining material and an end of the adhesive sheet is shorter than a distance between the lining material and an edge of the absorbent foam pad, and wherein a cross section of the lining material has a circular shape with a diameter equal to or smaller than a thickness of the adhesive sheet.

2. The wound dressing patch of claim 1, wherein the lining material is completely embedded within the adhesive sheet.

3. The wound dressing patch of claim 1, wherein the lining material is embedded within the adhesive sheet so that an outer peripheral surface of the lining material is surrounded by the adhesive sheet.

4. The wound dressing patch of claim 1, wherein the lining material is formed in a zigzag shape extending along the peripheral edge portion of the adhesive sheet.

5. The wound dressing patch of claim 1, wherein the lining material includes at least one curved portion.

6. The wound dressing patch of claim 1, wherein the lining material is attached to the one surface of the backing film, and at least a portion of an outer peripheral surface of the lining material is embedded within the adhesive sheet.

7. The wound dressing patch of claim 1, wherein the lining material includes at least one of a polymer selected from a group consisting of polyacrylamide, polypropylene, polyester, polyethylene, polyethylene terephthalate (PET), polystyrene, polyvinyl chloride (PVC) and polyacrylate, and a thermoplastic elastomer (TPE) for medical use.

* * * * *